United States Patent
Tanimoto et al.

(10) Patent No.: US 7,722,812 B2
(45) Date of Patent: May 25, 2010

(54) REACTION DISK AND SEPARATION CELL FOR AUTOMATIC ANALYZER

(75) Inventors: Kazuhito Tanimoto, Amagasaki (JP); Keiko Sasaki, Amagasaki (JP); Masayoshi Hayashi, Amagasaki (JP); Hishiri Komiyama, Amagasaki (JP)

(73) Assignee: Wako Pure Chemical Industries, Ltd., Ishikawa (JP)

( * ) Notice: Subject to any disclaimer, the term of this patent is extended or adjusted under 35 U.S.C. 154(b) by 0 days.

(21) Appl. No.: 10/581,695

(22) PCT Filed: Dec. 7, 2004

(86) PCT No.: PCT/JP2004/018209

§ 371 (c)(1),
(2), (4) Date: Jul. 11, 2006

(87) PCT Pub. No.: WO2005/057224

PCT Pub. Date: Jun. 23, 2005

(65) Prior Publication Data

US 2007/0087429 A1     Apr. 19, 2007

(30) Foreign Application Priority Data

Dec. 8, 2003  (JP) .............................. 2003-408523

(51) Int. Cl.
G01N 21/07    (2006.02)
G01N 9/30     (2006.02)
G01N 35/04    (2006.02)

(52) U.S. Cl. ............................. 422/64; 422/63; 422/72; 436/43; 436/45; 436/177; 356/246; 494/16

(58) Field of Classification Search ....................... None
See application file for complete search history.

(56) References Cited

U.S. PATENT DOCUMENTS

| 3,586,484 | A | * | 6/1971 | Anderson ...................... 436/45 |
| 3,681,029 | A | * | 8/1972 | Shapiro ........................ 422/104 |
| 3,759,666 | A | * | 9/1973 | Hill .............................. 435/14 |
| 4,612,873 | A | * | 9/1986 | Eberle .......................... 118/52 |
| 4,814,144 | A | * | 3/1989 | Edelmann et al. ........... 422/102 |
| 5,077,013 | A | * | 12/1991 | Guigan ......................... 422/64 |
| 5,422,018 | A | * | 6/1995 | Saunders et al. ............ 210/787 |
| 5,472,671 | A | * | 12/1995 | Nilsson et al. .............. 422/102 |
| 6,346,421 | B1 | * | 2/2002 | Anderson et al. ........... 436/177 |

FOREIGN PATENT DOCUMENTS

JP           57-171266         10/1982

(Continued)

Primary Examiner—P. Kathryn Wright
(74) Attorney, Agent, or Firm—Jordan and Hamburg LLP

(57) ABSTRACT

A reaction disk provides a compact and inexpensive design of an automatic analyzer so that the constituents in a suspension, such as blood sampled from a patient at a sick room or other place in a hospital, can be analyzed immediately and quantitatively. A separation cell and a determination cell are formed in a same reaction disk so as to maintain an upright position even during rotation of the both cells. The separation cell is formed to prevent poured suspension therein from flowing out during centrifugal separation, and a supernatant separated by centrifugation from the suspension contained in the separation cell is dispensed to the determination cell to analyze a target substance in the supernatant.

8 Claims, 5 Drawing Sheets

FOREIGN PATENT DOCUMENTS

| | | |
|---|---|---|
| JP | 59-210343 | 11/1984 |
| JP | 62-30377 | 7/1987 |
| JP | 3-175362 | 7/1991 |
| JP | 2731423 | 12/1997 |
| JP | 11-156243 | 6/1999 |
| JP | 11-311592 | 11/1999 |
| JP | 3060239 | 4/2000 |
| JP | 3192401 | 5/2001 |
| JP | 2002-541225 | 12/2002 |

* cited by examiner

REACTION DISK AND SEPARATION CELL FOR AUTOMATIC ANALYZER

TECHNICAL FIELD

The present invention relates to a reaction disk for an automatic analyzer which analyzes (determines) specified constituents in supernatant such as plasma and the like prepared by removing insoluble matter such as blood cells from a suspension such as blood and the like, and relates to a separation cell used in the reaction disk, specifically to a reaction disk and a separation cell to reduce the size of an automatic analyzer for determining the concentration of a target substance in plasma and the like.

BACKGROUND ART

Various types of analyzers for quantitatively analyzing constituents in a sample solution such as plasma have been brought into practical use.

Those types of conventional analyzers used to conduct separation of plasma and the like from whole blood by a preliminary treatment such as centrifugal separation and filtration, and conduct analysis of a sample solution such as thus separated plasma.

For the case of centrifugal separation, the separation cell was normally positioned in a tilted manner in the related art. Accordingly, when it came to add a function of centrifugal separation to the automatic analyzer, such type had to be adopted that a separation cell was mounted in a tilted manner, or a separation cell was of a swing type allowing the cell to tilt during the centrifugal separation. Owing to such configuration, a structure having both the separation cell and the reaction cell in a single disk became inevitably complex or the size thereof was increased due to disk installation therein. There were apparatuses having a separation disk and a reaction disk separately, which had drawbacks of failing to attain compact design and of increasing the cost.

DISCLOSURE OF THE INVENTION

Problems to be Solved by the Invention

It is highly convenient if the blood sampled from a patient at a sick room or other place in a hospital can be immediately separated to give plasma and the like, and can immediately and quantitatively analyze the constituents in the plasma and the like. To provide the analyzer with both the centrifugal separation function and the function to determine the specified constituents (reaction function), however, the conventional apparatuses become large, thus the conventional apparatuses were definitely unsuitable to use for the object.

Among the aspects of the present invention, a reaction disk is provided which can make the automatic analyzer inexpensive and small in size so that the constituents in a suspension such as blood sampled from a patient at a sick room or other place in a hospital can be quantitatively analyzed immediately.

Another aspect is to provide a separation cell which can potentially make the reaction disk inexpensive and small in size.

Means for Solving the Problems

Provision of the conventional separation cell and the conventional determination cell in a single reaction disk requires tilted mounting of the separation cell or adoption of a type which allows the cell to be tilted during rotation. That kind of configuration, however, increases the size of the apparatus and prevents integral molding of the disk, which increases the cost. Due to such reasons, there has been no practical arrangement having both the separation cell and the determination cell on a single disk in a completely independent manner of separation and determination.

To attain the above object, the inventors of the present invention conducted detail studies and found that it was possible to allow the separation cell to perform centrifugal separation in upright state similar to the rotary shaft and to arrange so that the suspension of blood or the like would not easily flow out from the separation cell even during the centrifugal separation in upright state, thus achieved the present invention of providing both the separation cell and the determination cell on a single reaction disk.

That is, according to an aspect of the present invention, a reaction disk comprises a separation cell and a determination cell provided in a same reaction disk keeping both cells in upright position even during rotation thereof, wherein the separation cell is formed to prevent a suspension from flowing out during centrifugal separation, and supernatant separated by centrifugation from the suspension contained in the separation cell is dispensed to the determination cell, thus enabling to analyze a target substance in the supernatant.

It is preferable that a single motor is arranged to change the rotational speed so as to rotate at a high speed for rotating the separation cell and at a low speed (for positioning) for rotating the determination cell, or a motor for separation and a motor for determination are arranged to be switched from each other.

It is preferable that the separation cell is provided with an insoluble matter collection zone and with a lid at an upper portion of the separation cell above the insoluble matter collection zone to partially cover the separation cell to prevent the suspension from flowing out during centrifugal separation.

Moreover, adding to the separation cell and the determination cell, the reaction disk further may comprise a dilution cell kept in upright position even during rotation, wherein the dilution cell is formed to prevent poured dilution solution therein from flowing out during centrifugal separation, and the dilution solution in the dilution cell is arranged to be dispensed to the determination cell enabling to dilute the supernatant. The reaction disk preferably is provided a lid at an upper portion of the dilution cell to partially cover the dilution cell to prevent the dilution solution from flowing out during centrifugal separation.

The separation cell for separating insoluble matter from suspension according to the present invention comprises a shelf provided in a cell, wherein an upper portion of the shelf is an insoluble matter collection zone, an lower portion of the shelf is a supernatant separation zone, the cell is provided with a lid at an upper part of the cell above the insoluble matter collection zone to partially cover the cell to prevent the suspension therein from flowing out during centrifugal separation, and the cell is used with keeping in upright position during centrifugal separation.

The separation cell is preferably formed by connecting the insoluble matter collection zone having a small cross sectional area with the supernatant separating zone having a large cross sectional area so that one side of the both zones are communicated with each other, the shelf is provided on the other side of the connecting part, and the upper part of the separation cell above the insoluble matter collection zone is covered partially by the lid.

The shelf provided in the separation cell is required to point toward the rotational center.

Effect of the Invention

According to an aspect of the present invention, both a separation cell and a determination cell are provided on a single reaction disk so as to keep their upright position even during rotation of the reaction disk. The configuration allows the automatic analyzer containing the reaction disk to be manufactured at low cost and in small size, which is highly preferable as an apparatus that immediately separates supernatant such as plasma from a suspension of blood and the like sampled from a patient at a sick room or other place, and that immediately analyzes the constituents in the supernatant.

Moreover, according to an embodiment of the present invention, it is possible to arrange easily so that the suspension is prevented from flowing out from the separation cell during centrifugal separation, and the supernatant can be separated even from a small volume of sample without allowing contaminating of insoluble matter. Accordingly, the separation cell can be formed at low cost and in small size.

The present invention is applicable to a suspension containing insoluble matter. That kind of suspension includes body fluid such as blood, excretion (such as fecal matter), sample derived from living body (such as sputum, pus, skin-derived substance, lymphocyte, blood cells, cell-derived substance, tissue-derived substance, pulverized matter thereof), environmental sample (such as food, drink, tap water, seawater, lake and marsh water, river water, industrial wastewater), plant-derived sample (such as plant tissue, cell, cultured matter thereof, pulverized matter thereof), microorganism-derived sample (such as various bacteria, viruses, cultured matter thereof, pulverized matter thereof), and suspension prepared by mixing these substances in water or buffer which is ordinarily adopted in this technical field, such as Tris buffer, phosphoric acid buffer, veronal buffer, boric acid buffer, and Good's buffer.

That is, the present invention is useful to eliminate insoluble matter from the above-described suspension, which insoluble matter includes blood cells, blood coagulation factor (such as fibrinogen, prothrombin, V-factor, and VIII factor), bloodplatelets, non-digestedmatter, cells, tissue, bacteria, viruses, and pulverized matter thereof, thus separating and collecting, for example, supernatant such as plasma, serum, various extracts, and culture supernatant. Specifically the present invention is useful to eliminate insoluble matter such as blood cells from blood, thus separating and collecting plasma, and to eliminate insoluble matter such as blood cells and several blood coagulation factors from blood, thus separating and collecting serum, and further specifically useful for separating and collecting plasma.

It is to be noted that for the case of separating plasma from blood, it is preferable to eliminate not only the blood cells but also the blood platelets as the insoluble matter. Nevertheless, complete elimination of blood platelets is not required if the quantity thereof does not affect the succeeding analysis.

BRIEF DESCRIPTION OF THE DRAWINGS

FIG. 2(B) shows a plan view of solely the reaction disk given in FIG. 2(A).

BEST MODES FOR CARRYING OUT THE INVENTION

Figure 1:
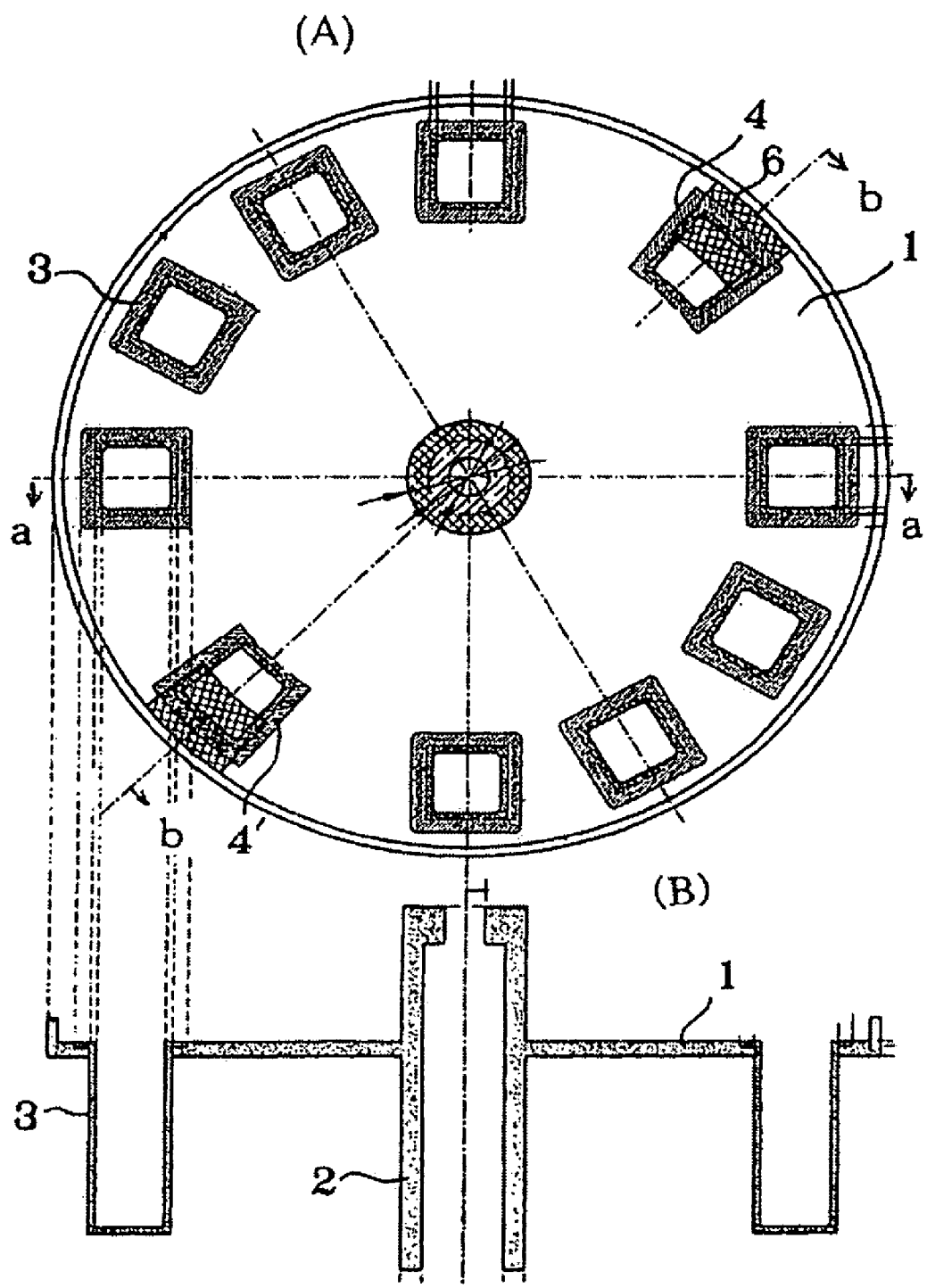
FIG. 1(A) shows a plan view of an example of reaction disk according to the present invention.
FIG. 1(B) shows a cross sectional view thereof along a-a line.

The embodiments of the present invention are described below referring to the drawings.

Figure 2:
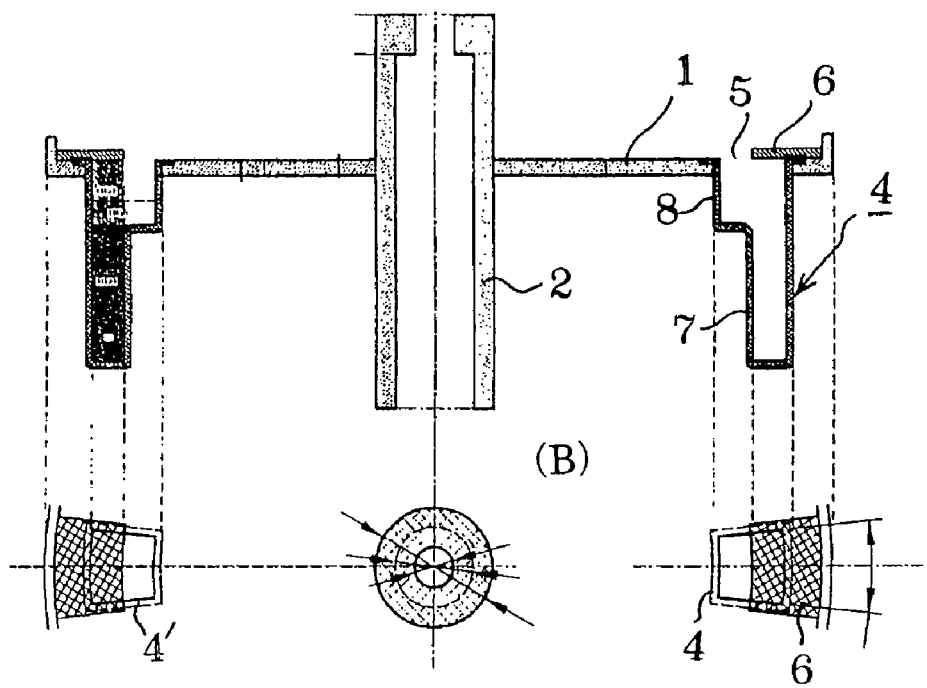
FIG. 2 (A) shows a cross sectional view along b-b line of FIG. 1(A)

FIGS. 1 and 2 show an example of the present invention. A circular-shape reaction disk 1 is formed rotatably around a rotary shaft 2 erecting at center thereof. Along the periphery of the reaction disk 1, there are arranged separating cells 4 and 4', opposing to each other, and a number of reaction cells (determination cells) 3, each cell being independently positioned and in upright state (vertical or substantially vertical position).

As illustrated in FIG. 1(B), the reaction cell 3 is provided in vertical position. If the reaction cell is provided in a tilted manner, maintaining the specified length of light pass in the reaction cell 3 becomes extremely difficult. The length of light pass in the reaction cell is required to be kept constant to execute the precise analysis and determination after the reaction.

As shown in FIG. 2(A), the separation cells 4 and 4' are also provided in vertical position. If the separation cell is provided in a tilted manner, the suction of supernatant after centrifugal separation becomes difficult, and in addition an extra space is required in the apparatus, which increases the size of the apparatus accordingly. Not only that but there are further arisen drawbacks such as decrease in efficiency of keeping the reaction cell 3 to a constant temperature, thereby causing trouble in positioning between the determination lamp and the light-receiving part, and difficulty in molding of the reaction cell and separation cell, thus increasing the cost.

A lid 6 is provided at a top opening of each of the separation cells 4 and 4', covering partially the opening 5. The reason for not covering the whole opening 5 of the separation cell is that a probe for dispensing the suspension and a probe for collecting the supernatant are to be inserted into the separation cell, (to secure a space for probe insertion). Accordingly, the lid 6 to partially cover the opening 5 may be the one that is a lid 6 having an opening to accept a probe to be inserted.

Figure 3:
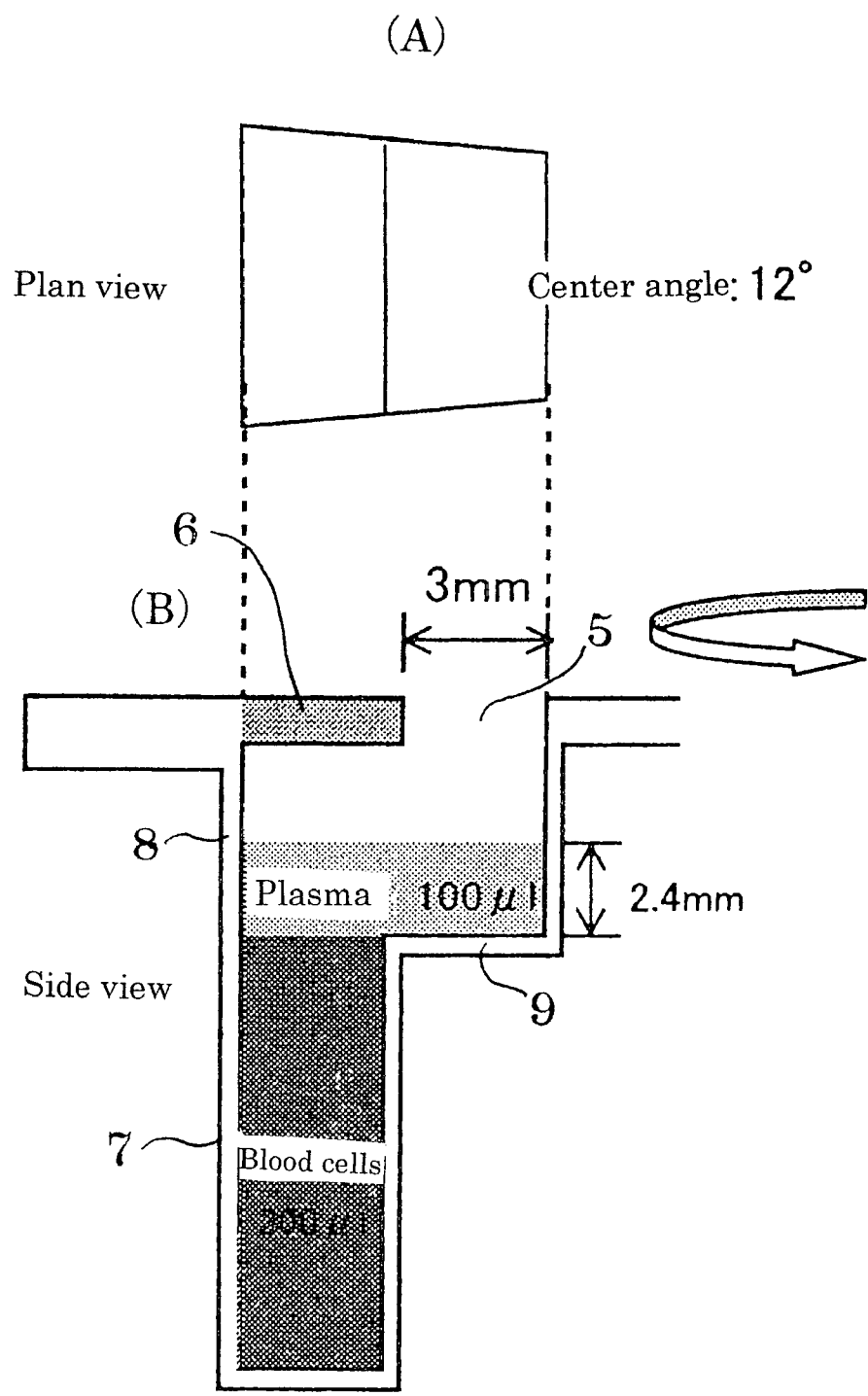
FIG. 3(B) shows a cross sectional view of an example of a separation cell according to the present invention.
FIG. 3(A) shows a plan view of a portion of the separation cell between the two dotted lines of FIG. 3(B).

As seen in FIG. 2 and FIG. 3, each of the separation cells 4 and 4' has a structure of an insoluble matter collection zone 7 having a small cross sectional area at lower part thereof and a supernatant separation zone 8 having a large cross sectional area at upper part thereof, connecting with each other to communicate, while forming a step, that is a shelf 9, at the connection part. The side surface of the insoluble matter collection zone 7 pointing towards the center of the disk 1 forms the step, while the opposite side surface thereof pointing outward of the disk 1 forms a flat face.

The lid 6 preferably has a size to cover at least the opening of the insoluble matter collection zone 7. The part of opening 5 which is not covered by the lid 6 is preferably at opposite side to the shelf 9, the reason of which is that it easily prevents the insoluble matter from flowing out during centrifugal separation. If the lid 6 has an opening to accept the insertion of probe, the opening is preferably positioned opposite to the shelf 9.

As illustrated in FIG. 2(B) and FIG. 3(A), the separation cells 4 and 4' are formed to have a cross section in fan-shape or trapezoidal shape. Although the shape of the separation cells is not necessarily in fan-shape or trapezoidal shape, the separation cells preferably have such a cross section as narrowing toward the center of disk 1. Having such an arrangement that the insoluble matter collection zone 7 is formed to be large to some degree, and thereby the supernatant separation zone 8 can accumulate only the supernatant, thus readily collecting fraction of the supernatant.

In the related art, for example, the sampled blood is subjected to centrifugal separation inclusive of a blood collecting vessel. Since the volume of the sampled blood is at least 5 ml, collecting the supernatant (such as plasma) of microliter order after the centrifugal separation is not so difficult. Some of the current blood collecting vessels have a function to let the separation agent enter easily between the blood cell and the plasma or the like, thus to prevent whirling up of blood cells. To realize small total size of the apparatus, the present invention intends to design the apparatus enabling to collect the supernatant from a sample volume of 400 μl level without trouble. Since the obtainable volume of plasma or the like from a sample of about 400 μl by separation is about 200 μl, the conventional separation cells have extreme difficulty in collecting plasma and the like without whirling up blood cells.

According to the present invention, since the shelf 9 is formed at the inward side [the side to which the blood cells (insoluble matter) are not pressed during centrifugal separation] of each of the separation cells 4 and 4', the sample held on the shelf 9 after the centrifugal separation is only the plasma and the like (supernatant), thereby achieving the prevention of whirling up of the blood cells and the like (insoluble matter) during collection of the supernatant.

When the suspension is treated by centrifugal separation with the configuration of vertical positioning of the separation cells 4 and 4' as the present invention, the insoluble matter gradually moves outward, while the supernatant gradually moves inward (to the center of the disk) during the centrifugal separation. Therefore, the shelf 9 has to be formed at inward side of the separation cells 4 and 4', (a side to which the insoluble matter is not pressed during centrifugal separation thereto). If the shelf 9 is to be formed at outward side of the separation cells 4 and 4', situation is the same as the case that the shelf 9 does not exist.

The lid 6 is not necessarily located at the top of the separation cell. However, since the separable volume of suspension depends on the position of the lid 6 and the total capacity of the insoluble matter collection zone 7 and the supernatant separation zone 8, the position of the lid 6 is preferably at the top of the separation cell for maximizing the capacity and also from consideration of easy cell molding. The capacity of the insoluble matter collection zone 7 is determined by the quantity of insoluble matter in the target suspension, and is required to have a volume not allowing the insoluble matter to enter the supernatant separation zone 8. The height of the shelf 9 is determined by the volume of the target suspension and by the quantity of the insoluble matter in the suspension.

For example, when the suspension is blood, the capacity of the blood cell (insoluble matter) collection zone 7 is decided by the difference of the hematocrit in the blood. Therefore the capacity is required to be defined so that the blood cell (insoluble matter) is accommodated in the insoluble matter collection zone 7 even in the case of blood showing high hematocrit.

Following is the description about the method for separating supernatant from suspension and -analyzing constituents in thus separated supernatant using the above reaction disk. Here, the analysis of target substance in the supernatant is described referring to an example case of determining the concentration of target substance.

Firstly, specified volume of suspension (blood, for example) was injected to each of the separation cells 4 and 4' shown in FIG. 1 and FIG. 2 through the opening 5 which is not covered by the lid 6 using a dispensing probe. After that, the motor was actuated to drive the rotary shaft 2 at high speed, thus executing the centrifugal separation.

Since the centrifugal force acted against the side face of the separation cell, not the bottom face thereof, the insoluble matter (blood cells, for example) gradually moved outward, while the supernatant (plasma, for example) gradually moved inward (to the center of the disk) during the centrifugal separation. Owing to the lid 6, no splashing out of the suspension (blood, for example) was observed during the centrifugal separation.

After stopping the motor, it was observed that the suspension was separated into the supernatant (plasma, for example) above the shelf 9 and the insoluble matter (blood cells, for example) below the shelf 9, as shown in FIG. 3. As illustrated in FIG. 3, the shelf 9 is required to be positioned at higher part than (or at least the same to) the boundary surface between the supernatant (plasma, for example) and the insoluble matter (bloodcells, for example).

Then, a dispensing probe was inserted through the opening 5 as illustrated in FIG. 3 to collect fraction of the supernatant (plasma, fore example) . Thus collected fraction was then dispensed in the reaction cell 3. Since the supernatant (plasma, fore example) was positioned above the shelf 9, whirling up of insoluble matter (blood cells, fore example) could be prevented.

A reagent disk (not shown) is located adjacent to the reaction disk 1. A dispensing probe 10 (refer to FIG. 4) reciprocates between the reagent disk and the reaction disk 1 to supply the reagent to the reaction cell 3. At that time, the reaction cell 3 is arranged to be transferred to a place where dispensing can be performed by dispensing probe 10 via a motor 18 when actuated.

The driving motor is arranged to rotate at high speed for rotating the separation cell and to rotate at a speed for positioning the disk to shift the determination cell position. To do this, a single motor may be used to vary the rotational speed, or a motor for centrifuging the separation cell and a motor for positioning the determination cell may be used to be switched from each other. According to the above example, a motor for high speed rotation (for separation) and a motor for positioning (for determination) are arranged to be switched from each other by a clutch so that either the rotary shaft of separation cell or the rotary shaft of determination cell rotates respectively. For instance, in the state that the clutch is engaged, the motor for high speed rotation drives the rotary shaft of the separation cell, while in the state that the clutch is disengaged, the motor for positioning drives the rotary shaft of the determination cell. In addition, for the case that a single motor is adopted to vary the rotational speed, the single driving motor is rotated at a high speed for rotating the separation cell and is rotated at a low speed for positioning the disk to shift the determination cell position, or the single motor does not vary the rotational speed but the rotational speed of the reaction disk may be varied by an adequate combination of gears, belts and the like in accordance with a conventional technique in the field.

Supply of the reagent induces a reaction between the supernatant (plasma, for example) and the reagent. According to a similar way to the related art, the optical density which was changed by the reaction is determined by a photometer shown in FIG. 4.

Figure 4:
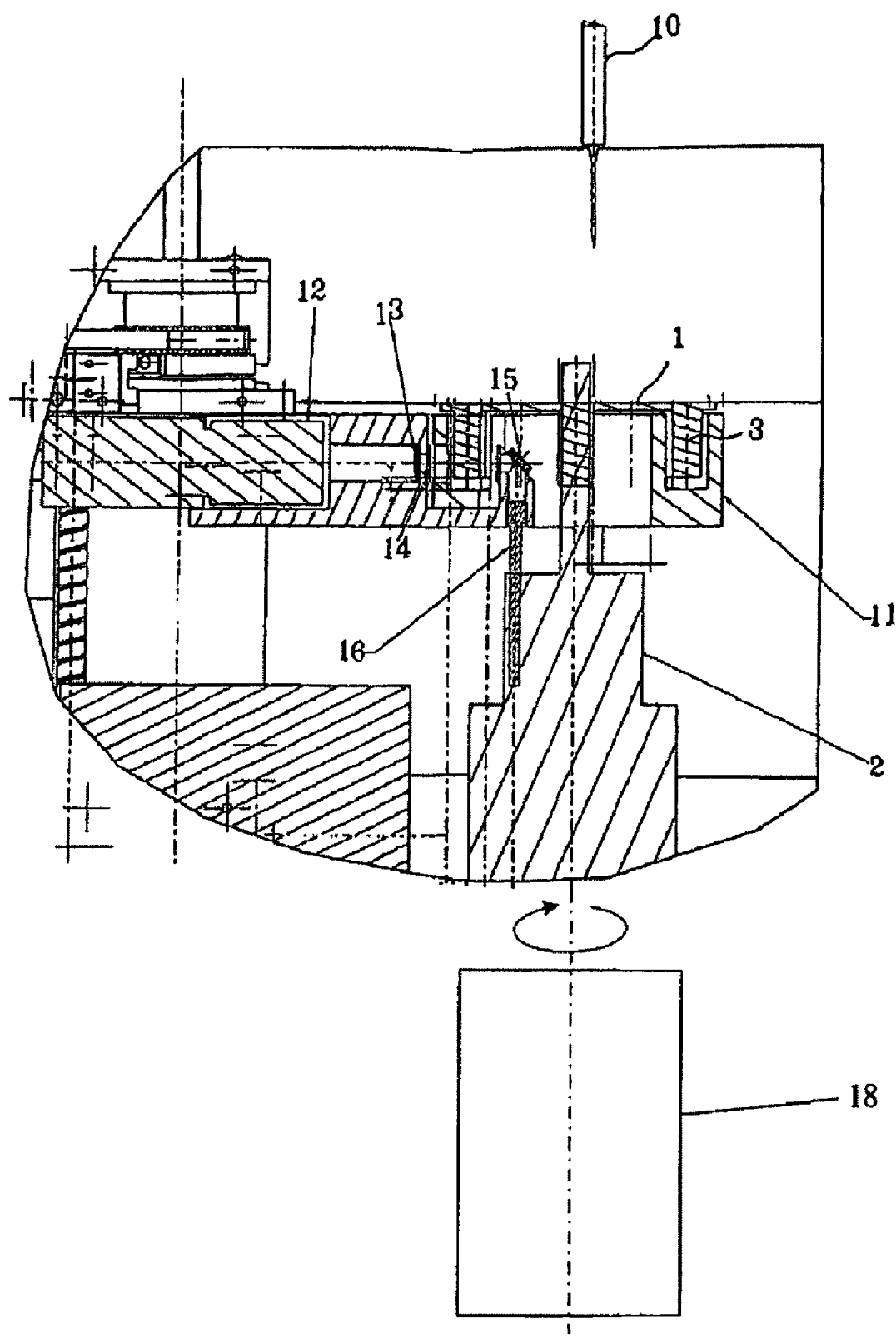
FIG. 4 shows a cross sectional view of an example of apparatus for determining optical density changed by the reaction between plasma and reagent.

In FIG. 4, the reaction cell 3 in the reaction disk 1 is installed in a reaction block (constant temperature container) 11 to maintain the reaction cell 3 at a specified constant temperature.

Light coming from a lamp 12 passes through a lens 13, and illuminates the reaction cell 3 through a light-irradiation window 14 in the reaction block 11, which then passes through the reaction cell 3 and reflects on a mirror 15. The light reflected on the mirror 15 is captured through a spectral zone fiber 16. The absorbance is derived from the data of thus captured light. The concentration of target substance is determined on the basis of the absorbance. The determination of the concentration of target substance is conducted in accordance with an ordinary technical method in the field, including the one using a standard, and the one using a calibration curve representing the relation between the absorbance and the concentration of the target substance, and the like.

Figure 5:
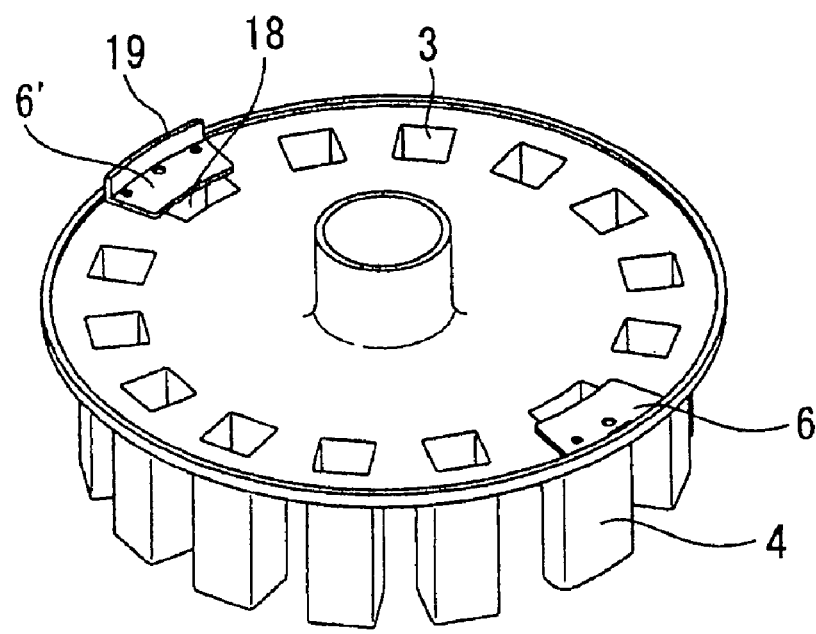
FIG. 5 shows a perspective view of another example according to the present invention.
Figure 6:
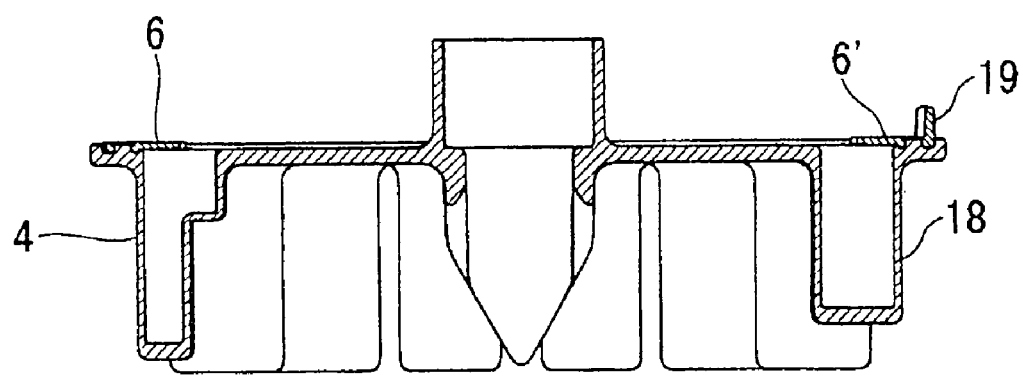
FIG. 6 shows a cross sectional view of FIG. 5.

FIG. 5 and FIG. 6 show another example of the present invention. A dilution cell 18 is independently provided in upright position (vertical or substantially vertical position) opposite to the separation cell 4. A specified volume of the supernatant separated in the separation cell 4 is poured in the reaction cell 3. The supernatant is diluted by a dilution solution in the dilution cell 18, if needed. Then a reagent is supplied to the reaction cell 13 to induce the reaction. If the dilution cell is provided in a tilted manner, there are arisen drawbacks similar to those observed in the case of tilt angle mount of the separation cell, including the difficulty in sucking the dilution solution, and the like. The dilution cell 18 has no step 9 which is observed in the separation cell 4 because the step is not specifically needed.

Although the dilution cell 18 is not necessarily located opposite to the separation cell 4, it is preferable to locate the dilution cell 18 opposite to the separation cell 4 for easily establishing the rotational balance of disk during centrifugal separation.

Moreover, it is preferable that the dilution cell 18 is formed considering the shape, the material, and other variables so that the weight (weight during the centrifugal separation) of the dilution cell containing the dilution solution (for the case of dispensing the dilution solution) and the weight (weight of separation cell 4 during the centrifugal separation) of the separation cell containing the suspension such as blood (the separation cell 4 with the dispensed suspension), become similar level with each other.

Note that, even if the supernatant separated in the separation cell 4 is not required to be diluted by the dilution solution, [i.e. even if the dilution cell 18 is not required, or even if the dilution cell 18 is not required to hold the dilution solution (not required to dispense)], due to the above described reason, the centrifugal separation may be performed via such an arrangement that the dilution cell 18 is disposed opposite to the separation cell 4 and the dilution solution is contained in (dispensed to) the dilution cell 18 so that the weight of the dilution cell with the dilution solution becomes similar to that of the separation cell holding the suspension such as blood therein(the separation cell 4 with the dispensed suspension).

The dilution solution includes water, physiological saline solution, and a buffer which is ordinarily adopted in this technical field, such as Tris buffer, phosphoric acid buffer, veronal buffer, boric acid buffer, and Good's buffer.

Similar to the separation cell 4, a lid 6' is located at the top opening of the dilution cell 18 to partially cover the opening. The reason for not covering the whole opening area of the dilution cell is that the opening allows a probe for dispensing the dilution solution to be inserted into the dilution cell (to secure a space for inserting the probe). Accordingly, the lid 6' partially covering the opening may be the one having an opening to accept the insertion of the probe, similar to the aforementioned case.

As illustrated in FIG. 5, the dilution cell 18 also has a cross section in fan-shape or trapezoidal shape. Although the section of the dilution cell is not necessarily in fan-shape or trapezoidal shape, the dilution cell preferably has such a cross section as narrowing toward the center of disk 1.

On the edge of the opposite side of the opening of the lid 6', there is formed a turn-up part 19 standing upright. The turn-up part 19 is not necessarily formed on the dilution cell 18, and it may be formed at least one position on the disk 1 such as, for example, on the opposite side edge of the opening of the lid 6 of the separation cell or at a determination cell.

The turn-up part 19 is for positioning of the disk 1, (for defining the starting point). A sensor (not shown) is located at a point on the periphery of the disk 1. When the disk 1 starts rotation, the sensor detects the turn-up part 19, thus letting the disk 1 stop at a specified position. The position of stopping the disk is defined as the starting point of the disk 1.

Since the apparatus cannot identify the position of the disk 1 immediately after installing the disk 1 or after centrifugal separation, the identification of the starting point is required. The turn-up part 19 is, for example, not necessarily required because the similar effect is obtained (starting point is determined) by other methods such as forming a wall of about 5 mm in height around the disk 1 while excluding the wall only at the portion of the dilution cell 10.

The phrase "analyzing the target substance in the supernatant" referred to herein includes the meaning of: determining (quantitatively analyzing) the amount of the target substance present in the supernatant; roughly determining (semi-quantitatively analyzing) the amount of the target substance; and detecting (qualitatively analyzing) the presence/absence of the target substance in the supernatant.

The analysis of target substance in the supernatant separated in accordance with the present invention may be conducted by ordinary methods such as chemical determination method, enzymological determination method, and immunological determination method, which are commonly applied in clinical test, biochemical, biomolecular, chemical, food, and other fields (for example, refer to International Publication Brochure No. 03/018614, and "Outline of Revision of Clinical Test Method", 2nd Print, 30th Edition, Dec. 20, 1993, Kanehara Publishing Co., Ltd.).

Also the reagent applied in the present invention may be the one commonly used in the above fields and methods, and may be adequately selected depending on the kind of the target substance and the method of analysis.

Description of the Reference Symbols

1 . . . reaction disk
2 . . . rotary shaft
3 . . . reaction cell (determination cell)
4, 4' . . . separation cell
5 . . . opening
6, 6' . . . lid
7 . . . blood cell collection zone
8 . . . plasma separation zone 9 . . . shelf
10 . . . dispensing probe
11 . . . reaction block
12 . . . lamp
14 . . . light-irradiation window
15 . . . mirror
16 . . . spectral zone fiber
17 . . . motor
18 . . . dilution cell
19 . . . turn-up part

The invention claimed is:

1. A reaction disk for an automatic analyzer, comprising:
a reaction disk body that is rotatable about a vertical axis;
at least one separation cell;
at least one determination cell, said at least one separation cell and said at least one determination cell being respectively arranged along a periphery of the reaction disk body located radially outward of said vertical axis, said at least one separation cell and said at least one determination cell being provided as discrete cell units which are independently separate from one another in said reaction disk body, at least a radially outward internal wall of each of said at least one separation cell and said at least one determination cell being maintained in a substantially parallel orientation with respect to said vertical axis when said reaction disk body is at rest and during rotation of said reaction disk body, supernatant separated by said centrifugal separation from the suspension contained in the separation cell being dispensable to the determination cell to allow analysis of a target substance in the supernatant; and
said at least one separation cell having an internal structure defining an insoluble matter collection zone in a lower portion of said at least one separation cell and a supernatant separation zone in an upper portion of said at least one separation cell, a horizontal sectional area of the supernatant separation zone being greater than another horizontal sectional area corresponding to said insoluble matter collection zone and a horizontal shelf is formed at the boundary between said supernatant separation zone and said insoluble matter collection zone where a portion of said supernatant separation zone extends radially inward of the insoluble matter collection zone, said shelf is orthogonal to a radially inward vertical wall of said insoluble matter collection zone; and
each said at least one separation cell including a lid being positioned to only partially cover each said at least one separation cell, said lid being disposed at a radially outward position of each said at least one separation cell directly over said horizontal sectional area corresponding to the insoluble matter collection zone, so as to leave an opening through which the supernatant is withdrawable from above said portion of said supernatant separation zone which extends radially inward of said insoluble matter collection zone, while concomitantly blocking flow of said suspension outward from said at least one separation cell during centrifugal separation.

2. The reaction disk according to claim 1, further comprising a single motor attached to the reaction disk body, a rotational speed of said single motor being selectable so as to rotate at a first speed for rotating said separation cell for carrying out said centrifugal separation of the suspension into said supernatant and an insoluble matter and at a second speed for rotatably positioning said determination cell at a place where dispensing is performable by a dispensing probe.

3. The reaction disk according to claim 1, further comprising a dilution cell kept in upright position even during rotation, wherein said dilution cell is formed to prevent poured dilution solution therein from flowing out during centrifugal separation, and said dilution solution in said dilution cell is arranged to be dispensed to said determination cell enabling to dilute said supernatant.

4. The reaction disk according to claim 3, wherein said dilution cell is provided with a lid at an upper portion of the dilution cell to partially cover said dilution cell to prevent the dilution solution from flowing out during centrifugal separation.

5. The reaction disk according to claim 1, wherein said suspension is blood containing blood cell as an insoluble matter, and said supernatant is plasma.

6. The reaction disk according to claim 1, wherein said reaction disk body is rotatably drivable at a speed suitable for separation and at another speed suitable for determination, said speed and said another speed being alternatively selectably appliable.

7. An automatic analyzer for a supernatant, comprising:
said reaction disk according to claim 1;
a dispensing probe for dispensing a reagent to said determination cell of said reaction disk;
a lamp that illuminates said determination cell; and
a motor for rotating said reaction disk body.

8. The automatic analyzer according to claim 7, wherein said suspension is blood containing blood cell as an insoluble matter, and said supernatant is plasma.

* * * * *